US006206921B1

(12) United States Patent
Guagliano et al.

(10) Patent No.: US 6,206,921 B1
(45) Date of Patent: *Mar. 27, 2001

(54) METHOD OF REPLACING NUCLEUS PULPOSUS AND REPAIRING THE INTERVERTEBRAL DISK

(76) Inventors: Peter A. Guagliano, 370 Bay Ridge Pkwy., Brooklyn, NY (US) 11209; Anthony C. Ross, 3546 Maybank Hwy., John's Island, SC (US) 29455

( * ) Notice: Subject to any disclaimer, the term of this patent is extended or adjusted under 35 U.S.C. 154(b) by 0 days.

This patent is subject to a terminal disclaimer.

(21) Appl. No.: 09/255,372

(22) Filed: Feb. 22, 1999

(51) Int. Cl.[7] ....... A61F 2/44

(52) U.S. Cl. ....... 623/17; 606/92

(58) Field of Search ....... 606/92, 93, 94; 623/17; 128/898

(56) References Cited

U.S. PATENT DOCUMENTS 5,047,055 * 9/1991 Bao et al. ....... 623/17
5,545,229 * 8/1996 Parsons et al. ....... 623/17
5,800,549 * 9/1998 Bao et al. ....... 623/17

* cited by examiner

*Primary Examiner*—Michael Buiz
*Assistant Examiner*—Julian W. Woo
(74) *Attorney, Agent, or Firm*—Browning Bushman

(57) ABSTRACT

A process for repairing the annulus fibrosus, and replacing the nucleus pulposus. Removal of the nucleus pulposus and only as much of the annulus fibrosus and intervertebral disk as necessary is performed. The tissue so removed is replaced by a material which is resilient, but non-dispersing upon setting. After application of the material, and after the material is set, the resiliency of the material permits motion of the vertebrae and performs the cushioning and joint functions of the intervertebral disk. The material is physiologically acceptable to the human body.

18 Claims, 2 Drawing Sheets

12
4
6
8
10

METHOD OF REPLACING NUCLEUS PULPOSUS AND REPAIRING THE INTERVERTEBRAL DISK

FIELD OF THE INVENTION

This invention relates to surgical methods generally, and is more specifically related to a process of repairing the intervertebral disk of mammals.

BACKGROUND OF THE INVENTION

Intervertebral disks are prone to injury. Due to the low blood supply to this area, intervertebral disks are slow to heal, and may not materially heal. When the annulus fibrosus is torn, or punctured, the nucleus pulposus can migrate. A ruptured/prolapsed annulus fibrosus is demonstrated in FIG. 1. A mechanical translation of the disk material is demonstrated in FIG. 2.

Annulus fibrosus, as referred to herein, is the marginal or peripheral portion of an intervertebral disk. The intervertebral disk is a disk with fibrous bands surrounding the nucleus pulposus occupying the space between two vertebra. The anatomy of the disk provides a cushion to allow motion, limit motion and provide space, distancing the vertebra off the nerves and compressible tissue. Part of the vertebrae are bony blocks, which, when stacked one upon the other, form the anterior portion of the spine. Annulus fibrosus is also known as annulus fibrosus disci intervertebralus. The nucleus pulposus is a substance of jelly-like consistency found in the center of a intervertebral disk.

The effect of a ruptured/prolapsed annulus fibrosus may result in spasm, and neurological compromise, such as the compressed nerve indicated in FIG. 1 and other compressible soft tissues, i.e. arteries, veins. Degeneration of the condition may increase over time, resulting in chronic and debilitating pain. The condition is usually disabling.

Suppressive measures include steroidal injection, removal of the nucleus pulposus, and fusion either by donor bone, coral or by metal bracing. If disk removal is performed, a healthy part of the disk is often taken, eradicating the function of the joint, and accelerating the degeneration of adjacent segments of the body, as the body attempts to stabilize. This approach frequently leaves the patient immunologically and structurally compromised, if not permanently disabled.

Isolated treatment to only the damaged structures employing the most noninvasive procedure possible is preferred. This approach allows as much of the healthy tissue as possible to remain, and to retain normal neurological function. While the offending material can be removed, the material must be replaced with a material which will perform the function formerly performed by the material removed. A need exists for a process which limits the material removed from the intervertebral disk, and which replaces the material so removed with a composition that is physiologically acceptable to the human body, and which allows the intervertebral disk to retain motion and characteristics of normal joint function, including cushioning the joint as compression is introduce from the stacking of the vertebrae. The material must be pliable in its application, and non-dispersing after replacement.

SUMMARY OF THE PRESENT INVENTION

The present invention is a process of repairing the disk through replacing the nucleus pulposus. The process of the invention desires minimal invasiveness. Motion within the vertebrae, and joint function and cushioning in the intervertebral disk, are regained by the process.

The process involves removal of the nucleus pulposus and only as much of the annulus fibrosus and intervertebral disk as is necessary. The tissue so removed is replaced by a material which is resilient and non-dispersant upon setting, and within a temperature range of 35° and 42° C. After application of the material, and after the material is set, the resiliency of the material permits motion of the vertebrae, and performs the cushioning and joint functions of the intervertebral disk. The material is physiologically acceptable to the human body.

DETAILED DESCRIPTION OF THE PREFERRED EMBODIMENT

The rupture/prolapse of the annulus fibrosus is first identified and isolated. This identification and isolation is by means such as x-ray, MRI or other diagnostic imaging procedures which are diagnostically acceptable. After the area of rupture/prolapse is identified and isolated, the site is surgically accessed. Since it is a goal of the invention to minimize trauma associated with the procedure, it is preferred to access the site through an arthroscopic procedure, or technology that involves minimal invasion and offense to healthy areas of the annulus fibrosus, while damaged parts of the intervertebral disk are removed. Current technology allows for surgical removal of nucleus pulposus via irrigation and suction.

The material removed is replaced with a resilient material which physiologically acceptable to the human body. The material is first prepared so that it will have molten or semi-solid properties which allow transportation of the material to the site.

Figure 1:
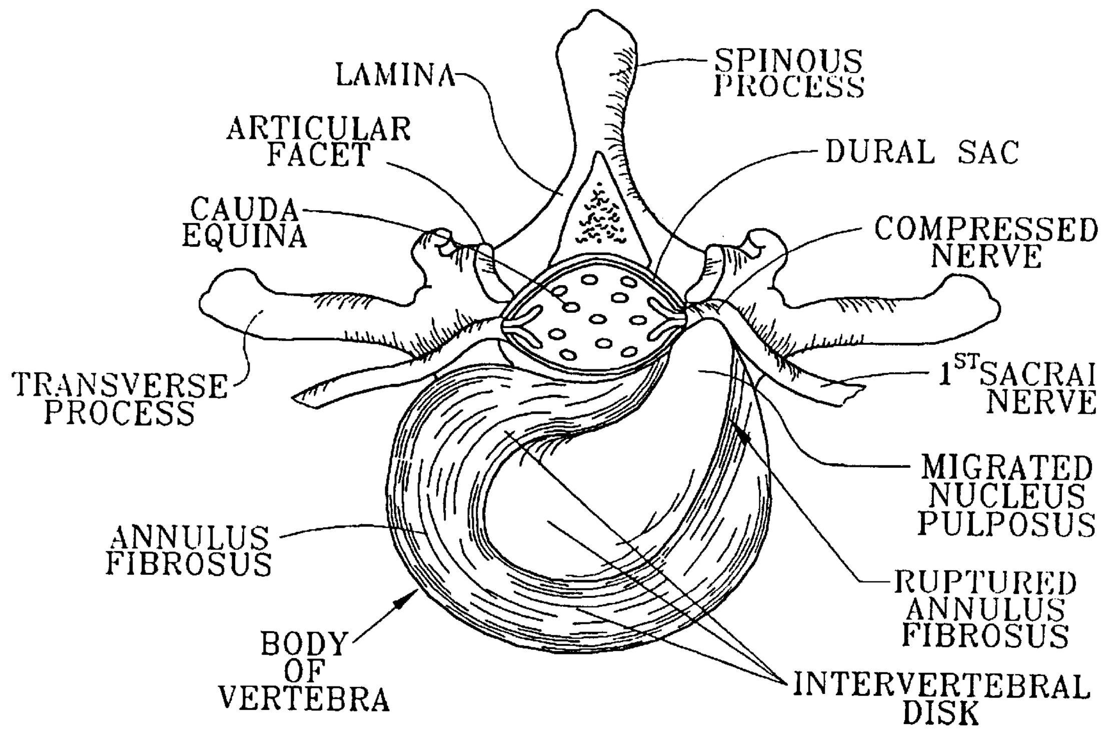
FIG. 1 shows, inter alia, a ruptured/prolapsed annulus fibrosus and the resulting migrated nucleus pulposus of an intervertebral disk.
Figure 2:
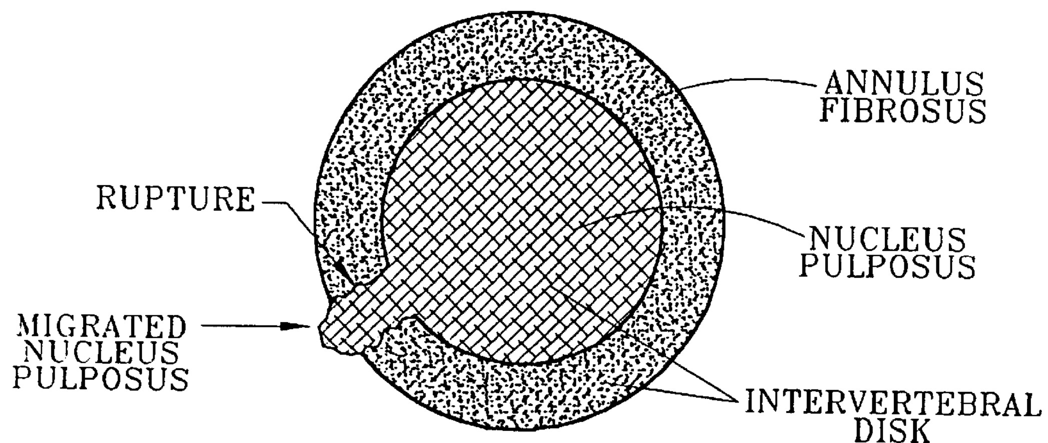
FIG. 2 demonstrates mechanical translation of a ruptured/prolapsed annulus fibrosus.
Figure 3:
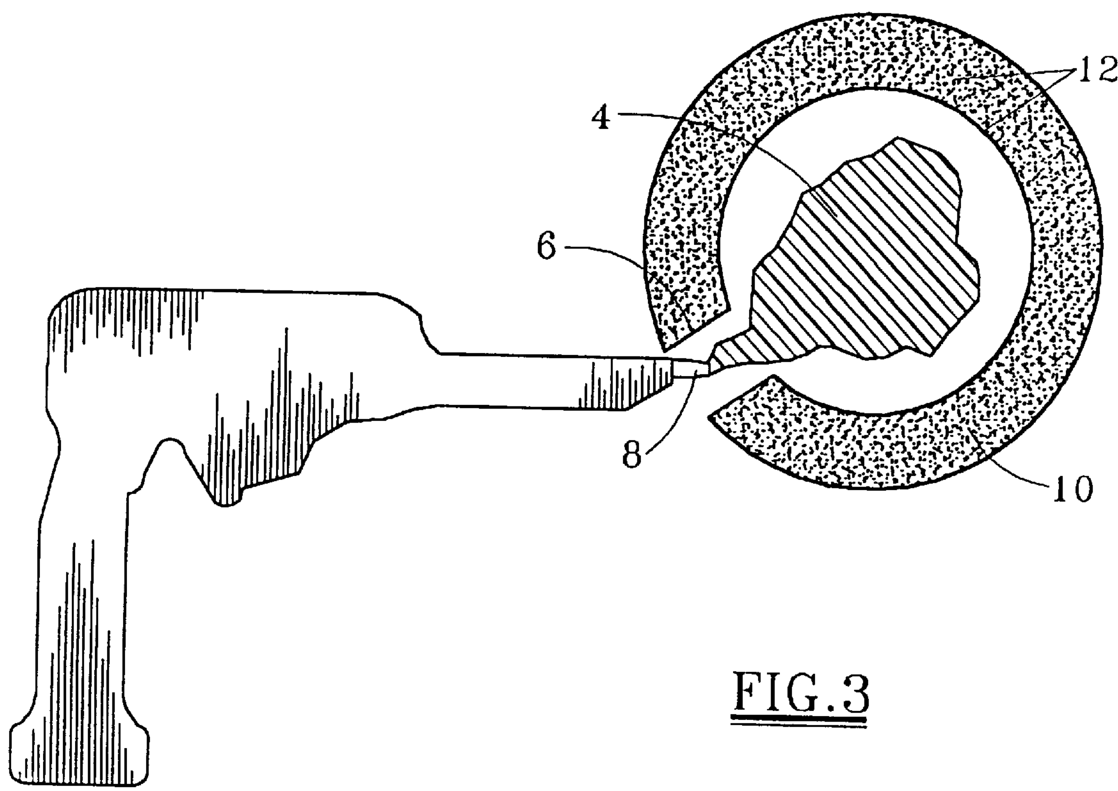
FIG. 3 demonstrates the replacement of the nucleus pulposus and the ruptured/prolapsed portion of the annulus fibrosus by the introduction of gutta percha via a mechanically facilitating device.
Figure 4:
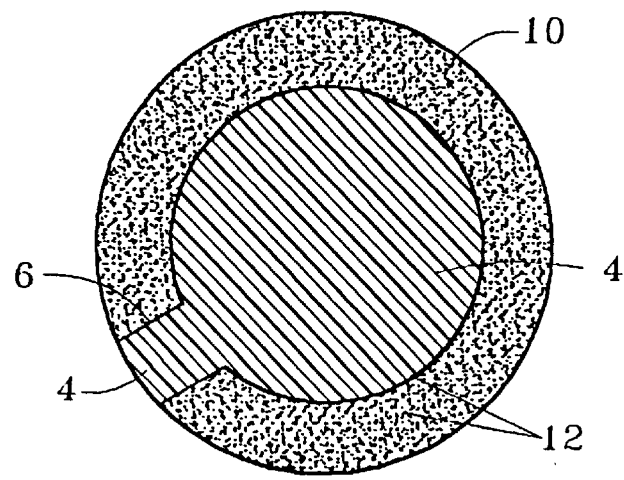
FIG. 4 demonstrates the intervertebral disk after repair with gutta percha.

In the preferred embodiment, the material used for replacement of removed tissue is gutta percha. Gutta percha is a geometric isomer of natural rubber. When cold, gutta percha is relatively inelastic, but as it warms, it becomes moldable. At a high temperature, gutta percha will melt sufficiently to allow transportation of the material. Accordingly, the gutta percha is prepared by heating it to a sufficient temperature to melt the gutta percha. The gutta percha is then injected via mechanically facilitated means into the site, FIG. 3, replacing the tissue which has been surgically removed. The gutta percha may be transported into the site by means of an applicator 2 which applies pressure and directs the material through a nozzle 8 which may utilize insulated properties of ceramics. Dental gutta percha is reported to contain approximately 19–22% gutta percha, 1–4% plasticizing waxes and resins, 59–75% zinc oxide, 1–17% metal sulfates for radiopacity and trace amounts of organic dyes for coloration.

The applicator is designed to maintain the temperature of the gutta percha above ambient temperature so that the gutta percha flows, while also providing pressure control, which allows the gutta percha to be directed, and the flow volume and pressure controlled.

The gutta percha 4 replaces the nucleus pulposus and the affected area 6 of the annulus fibrosus 10, and, as applicable, the intervertebral disk 12. The volume of the removed tissue is replaced. Tractioning of the joint to create a negative (relative to ambient) pressure, to facilitate spacing and flow, may be employed.

As the gutta percha cools, the gutta percha will set. At normal human body temperatures, the gutta percha is no longer moldable, and it is not migratory. Accordingly, the gutta percha will remain in the site, filling the area formerly occupied by the nucleus pulposus, and repairing the rupture/prolapsed annulus fibrosus and associated migrated nucleus pulposus. The gutta percha is sufficiently resilient to restore the partial function previously performed by the intervertebral disk of cushioning a joint between the associated vertebrae.

If necessary, gutta percha may be subsequently removed from the site via surgical, physical, enzymatic and/or chemical means.

What is claimed is:

1. A process of replacing nucleus pulposus of an intervertebral disk, comprising the steps of:

a. identifying a location of a prolapse in an annulus fibrosus of an intervertebral disk;

b. removal of nucleus pulposus contained in said annulus fibrosus of said intervertebral disk;

c. injection of a resilient material comprising a geometric isomer of natural rubber which will not disperse upon setting, so as to cause said resilient material to occupy a space formerly occupied by said nucleus pulposus.

2. The process of replacing nucleus pulposus of an interverbral disk as described in claim 1, wherein nucleus pulposus is removed prior to injection of said resilient material.

3. The process of replacing nucleus pulposus of an intervertebral disk as described in claim 1, wherein said resilient material comprises dental gutta percha.

4. The process of replacing nucleus pulposus of an intervertebral disk as described in claim 2, comprises dental gutta percha.

5. The process of replacing nucleus pulposus of an intervertebral disk as described in claim 1, wherein the resilient material comprises gutta percha and zinc oxide.

6. The process for replacing nucleus pulposus of an intervertebral disk as described in claim 5, wherein the resilient material comprises approximately 19 to 22% gutta percha and 59 to 75% zinc oxide.

7. The process for replacing nucleus pulposus of an intervertebral disk as described in claim 5, wherein the resilient material further comprises plasticizing waxes and resins.

8. The process of replacing nucleus pulposus of an intervertebral disk as described in claim 5, wherein the resilient material further comprises metal sulfates.

9. The process of replacing nucleus pulposus of an intervertebral disk as described in claim 1, further comprising:

heating the resilient material prior to injection of the resilient material.

10. The process of replacing nucleus pulposus of an intervertebral disk as described in claim 9, further comprising:

pressurizing the heated resilient material to inject the resilient material into the intervertebral disk.

11. The process of replacing nucleus pulposus of an intervertebral disk as described in claim 9, wherein said heated resilient material is injected through a nozzle and then into the space formally occupied by the nucleus pulposus.

12. The process of replacing nucleus pulposus of an intervertebral disk as described in claim 1, wherein removal of nucleus pulposus comprises irrigation and suction.

13. A process of replacing nucleus pulposus of an intervertebral disk, comprising the steps of:

a. identifying a location of a prolapse in an annulus fibrosis of an interverbral disk;

b. heating a resilient material;

c. pressurizing the heated resilient material and injecting the resilient material into the intervertebral disk, such that the injected heated material will set and occupy a space formerly occupied by said nucleus pulposus.

14. The process of replacing nucleus pulposus of an intervertebral disk as described in claim 2, wherein said resilient material comprises dental gutta percha.

15. The process of replacing nucleus pulposus of an intervertebral disk as described in claim 13, wherein said resilient material comprises dental gutta percha.

16. The process for replacing nucleus pulposus of an intervertebral disk as described in claim 13, wherein the resilient material comprises approximately 19 to 22% gutta percha and 59 to 75% zinc oxide.

17. The process of replacing nucleus pulposus of an intervertebral disk as described in claim 13, wherein said heated resilient material is injected through a nozzle and then into the space formally occupied by the nucleus pulposus.

18. The process of replacing nucleus pulposus of an interverbral disk as described in claim 13, further comprising:

nucleus pulposus removing in the interverbral disk prior to injecting the heated material.

* * * * *

UNITED STATES PATENT AND TRADEMARK OFFICE

CERTIFICATE OF CORRECTION

PATENT NO. : 6,206,921 B1
DATED : March 27, 2001
INVENTOR(S) : Peter A. Guagliano et al.

It is certified that error appears in the above-identified patent and that said Letters Patent is hereby corrected as shown below:

Column 3,
Line 43, after "Claim 2" insert -- wherein said resilient material --.

Signed and Sealed this

Thirtieth Day of October, 2001

*Attest:*

Nicholas P. Godici

NICHOLAS P. GODICI

*Attesting Officer*

*Acting Director of the United States Patent and Trademark Office*